United States Patent
Russell

(10) Patent No.: US 7,183,552 B2
(45) Date of Patent: Feb. 27, 2007

(54) OPTICAL SYSTEM FOR A GAS MEASUREMENT SYSTEM

(75) Inventor: James T Russell, Bellevue, WA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 10/792,180

(22) Filed: Mar. 3, 2004

(65) Prior Publication Data

US 2004/0256560 A1    Dec. 23, 2004

Related U.S. Application Data

(60) Provisional application No. 60/452,656, filed on Mar. 7, 2003.

(51) Int. Cl.
  *G01N 21/00* (2006.01)
(52) U.S. Cl. .................................. 250/338.5
(58) Field of Classification Search .............. 250/338.5
  See application file for complete search history.

(56) References Cited

U.S. PATENT DOCUMENTS

| | | | |
|---|---|---|---|
| 4,622,464 A * | 11/1986 | Sukigara et al. ............ 250/343 |
| 5,282,473 A | 2/1994 | Braig et al. | |
| 5,341,214 A * | 8/1994 | Wong .......................... 356/437 |
| 5,369,277 A | 11/1994 | Knodle et al. | |
| 5,616,923 A | 4/1997 | Rich et al. | |
| 5,693,944 A | 12/1997 | Rich | |
| 6,369,387 B1 * | 4/2002 | Eckles ......................... 250/343 |
| 6,410,918 B1 * | 6/2002 | Kouznetsov ................ 250/343 |
| 2001/0048079 A1 * | 12/2001 | Brunamoti et al. ......... 250/343 |
| 2002/0153490 A1 * | 10/2002 | O'Leary ...................... 250/353 |

* cited by examiner

*Primary Examiner*—David Porta
*Assistant Examiner*—Marcus Taningco
(74) *Attorney, Agent, or Firm*—Michael W. Haas

(57) ABSTRACT

An improved optical configuration for use in a gas monitoring system. The optical system uses a high numerical aperture lens that maximizes capture of relatively large angle rays, thereby increasing the measured signal at the infrared radiation detector. In one embodiment of the present invention, a half-ball-type lens is provided proximal to the infrared radiation source in the gas measurement system. To further increase the measured signal at the infrared radiation detector and allow more efficient capture of the larger angle rays, materials that are reflective in the infrared band of interest are used, so that the walls of the sample cell act as a hollow light pipe.

4 Claims, 6 Drawing Sheets

OPTICAL SYSTEM FOR A GAS MEASUREMENT SYSTEM

CROSS-REFERENCE TO RELATED APPLICATIONS

This application claims priority under 35 U.S.C. § 119(e) from provisional U.S. patent application No. 60/452,656 filed Mar. 7, 2003, the contents of which are incorporated herein by reference.

BACKGROUND OF THE INVENTION

1. Field of the Invention

The present invention pertains to a gas measurement system, and, in particular, to a gas measurement system having an improved optical system, and to a method of using such a system.

2. Description of the Related Art

It is well-known to those skilled in the art that non-dispersive infrared (NDIR) type gas analyzers operate on the principle that the concentration of specific gases, such as carbon dioxide, nitrous oxide, and anesthetic agents, can be determined by (a) directing infrared radiation from an infrared emitter through a sample of a gaseous mixture, (b) filtering this infrared radiation to minimize the energy outside the band absorbed by the specific gases, (c) measuring the radiation impinging upon an infrared radiation detector and which has passed through this sample, and (d) relating a measure of the infrared absorption of the gas to a gas concentration. Gases that may be measured exhibit increased absorption (and reduced transmittance) at specific wavelengths in the infrared spectrum. Moreover, the greater the gas concentration, the greater the infrared absorption and the lower transmittance.

Also well-known to those skilled in the art are dispersive infrared (DIR) gas analyzers, which operate on the principle that the concentration of specific gases can be determined by (a) directing infrared radiation from an infrared emitter through a sample of a gaseous mixture, (b) separating the received radiation into a discrete number of wavelengths in a wavelength band of interest using a prism or grating, (c) measuring the radiation of each wavelength impinging upon a infrared radiation detector and which has passed through this sample, and (d) relating measures of the infrared absorption determined at each of the wavelengths to at least one gas concentration.

NDIR gas analyzers are widely used in medical applications and can be characterized as either disposed in the main path of the patient's respiratory gases, known as mainstream or non-diverting gas analyzer, or located off of the main path, known as sidestream or diverting gas analyzer. DIR gas analyzers are used in some medical applications but presently only sidestream gas analyzers are available.

Regardless of whether the analyzer diverts gas from the main gas flow path or not, the gas to be analyzed must travel through a flow passage in which infrared radiation passes through the gas sample. This portion of the passage, generally known as a sample cell, confines a sample composed of one or more gases to a particular flow path that is traversed by the optical path between the infrared radiation source assembly and the infrared radiation detector assembly. Strictly speaking, the sample cell refers only to the portion of the flow path through which infrared radiation passes. However, the sample cell is also referred to the airway adapter by those in the industry and the terms can be used interchangeably.

The infrared radiation source assembly and the infrared radiation detector assembly are both components of a transducer that may be detachably coupled to the sample cell. Also note that the physical relationship between the optical path and flow path depends upon the specific design of the sample cell. At least one optical aperture in the wall of the sample cell permits infrared radiation to traverse the sample cell. A transmissive window located in each optical aperture confines the gases to the sample cell flow passage and keeps out foreign matter, while minimizing the loss of infrared energy as the infrared beam enters and exits from the sample cell through the transmissive window or windows.

The distance traversed by the infrared radiation in the flow passage of the sample cell is known as the measurement path length. In a sample cell where the optical windows are located on opposite sides of the sample cell, the measurement or optical path length is the distance between the optical apertures of the sample cell. In a sample cell with a single optical window and an infrared reflective mirror, the path length is twice the distance between the optical window and the mirror. At a constant partial pressure or concentration of a gas, as the optical path length increases, a greater quantity of the emitted infrared radiation is absorbed at the wavelength(s) specific to the gas of interest due to the presence of a greater number of molecules of the gas of interest along the optical path. The infrared absorbance can be quantified using Beer's Law, which includes a term for the measurement path length. With a ratiometric measurement approach known in the NDIR art, the ratio of two concurrent measurements, the measured radiation at wavelengths specific to the gas interest, known as the data channel value, and the measured radiation at other wavelengths where little or no absorption occurs, known as the reference channel value, allows the partial pressure of the gas to be determined. Thus, to achieve an acceptably low noise and a fast response time for the gas analyzer, the tradeoffs between the measurement path length and volume of the sample cell must be carefully considered in any sample cell design.

Mainstream gas analyzer designs require that the optical and/or electronic components interface with the subject's airway or respiratory circuit. A mainstream analyzer is typically situated such that the patient's inspired and expired respiratory gases pass through the sample cell onto which a transducer, which includes elements necessary for monitoring respiratory gases, is placed. Typically, the optical path in a mainstream system traverses the flow path, with optical apertures being provided in the wall of the sample cell and aligned along and on opposite sides of the flow passage. This configuration allows the beam of infrared radiation to enter the sample cell, traverse the gases in the flow passage, and, after being attenuated, exit from the sample cell to the infrared detector assembly, which is comprised of optical components to direct the infrared radiation and components to detect the radiation.

In an NDIR type gas analyzer, the detection components include narrow band filters and infrared radiation detectors. In DIR type gas analyzers, the detection components comprise a spectrometer as known in the art. Often such designs have sample cell optical apertures of a constant size that are set by each manufacturer and that are sufficiently large so as not to restrict the beam of infrared radiation. These designs provide an adequate resolution and accuracy for clinical measurements provided that the optical path length is sufficient to enable an adequate signal to be measured even in the presence of a relatively high absorbance, i.e., low transmittance. However, the introduction of different removable sample cells, often with different sized optical apertures for applications requiring lower sample cell volumes (such as pediatric and neonatal monitoring, and sidestream adapters used with mainstream transducers), caused a reduction and offset in the signals measured by the infrared radiation detectors. The observed differences between the different types of sample cells that are used with the same transducer have been termed the "bias" problem, and have hampered progress for improved device performance and seamless interchangeability of sample cells with differently sized optical apertures.

In sidestream analyzer designs, the optical and electronic components are typically positioned at a distance away from the subject's airway or respiratory circuit in communication therewith. U.S. Pat. No. 5,282,473, issued to Braig et al., discloses an exemplary sidestream infrared gas analyzer and sample cell. Sidestream gas analyzers typically communicate with a patient's airway by way of a long sampling tube connected to an adapter, e.g., a T-piece at the endotracheal tube or mask connector positioned along a breathing circuit or a nasal catheter that has been placed in communication with the patient's airway. As the patient breathes, gases are continuously drawn at sample flow rates ranging from 50 to 250 ml/min from the breathing circuit through the sampling tube and into the sample cell located within or near the monitor. The physical relationship between the optical path and flow path for sidestream sample cells varies and depends upon the specific manufacturer. Thus, differences in the sample cell's optical path length will impact the sensitivity and optimal operating range of the system.

In the designs from most manufacturers, the optical path in a sidestream system transverses the flow path, with optical apertures being provided in the wall of the sample cell and aligned along and on opposite sides of the flow passage. In other designs, the flow path is more circuitous, so that the optical aperture can be positioned such that the infrared radiation passes through the gas parallel to the direction of gas flow. In such designs, the optical path length may be much greater than in a conventional transverse design. In both sidestream sample cell designs, the sample cell volume defines the amount of gas that needs to be cleared in order for the system to respond to the changes in the sample. In order for an adequate response time to be obtained, this volume must be minimized. Therefore, it is desirable that the beam of infrared radiation that passes through the flow path be narrow and that energy losses are minimal, so that a sufficient signal can be received at the infrared radiation detectors. A sample cell with a large path length, hence high sensitivity, and a small cross section to keep the volume small, can satisfy these requirements.

A number of commercially available mainstream and sidestream gas analyzers employ an infrared source consisting of an infrared emitter and a polished, parabolic, mirror surface formed in the surface which the emitter faces. U.S. Pat. No. 5,369,277 issued to Knodle et al. discloses an exemplary infrared source, as shown in FIG. 1. Mirror 10 collimates the emitted infrared radiation source rays from infrared radiation source 20 and focuses the collimated rays into a beam that is directed along the optical path of the device. The infrared source rays pass through an optical aperture containing an infrared transmissive window, enter one end of the sample cell, and those that are parallel, or nearly parallel, i.e. having a small angle relative to parallel, to the axis of the optical path through the sample cell, pass out the aperture at the other end of the sample cell into the detector. In conventional sample cells, rays that enter at a larger angle relative to the axis of the optical path may be stopped by the aperture at the detector end of the cell. In practice, the length to cross section ratio is large, so that a relatively small number of rays are able to get though to the detector.

With the development of devices using different sized sample cells with smaller apertures, a need exists to reduce the source energy lost in the sample cell, and the associated loss in signal level from the radiation detector. Methods to reduce the amount of source energy lost through large angle rays are sought, thereby improving the signal/noise ratio and performance of such devices.

SUMMARY OF THE INVENTION

Accordingly, it is an object of the present invention to increase the measured signal at the infrared radiation detector with an optical design using a high numerical aperture to allow the capture of a greater number of large angle rays, thereby overcoming the shortcomings of conventional infrared gas measurement system optical designs. This object is achieved according to one embodiment of the present invention by providing a half-ball-type lens in close proximity of the infrared radiation source.

It is yet another object of the present invention to further increase the measured signal at the infrared radiation detector by allowing more efficient capture of the larger angle rays by using materials that are reflective in the infrared band of interest so that the walls of the sample cell act as a hollow light pipe.

While the use of infrared radiation has been described, the principles of the present invention are also applicable to measurement systems using sources emitting other wavelengths bands including but not limited to visible and ultra-violet radiation.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
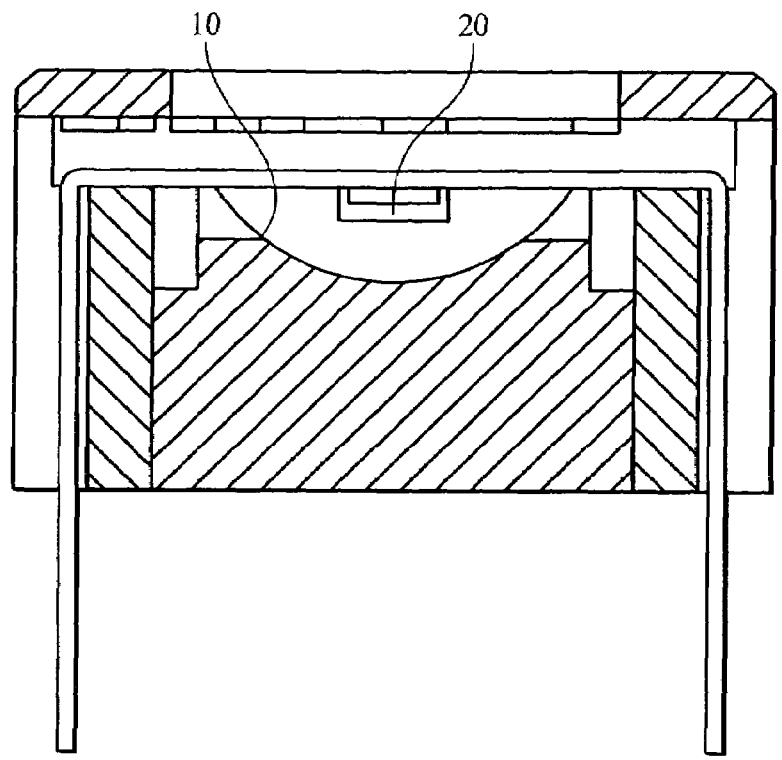
FIG. 1 is cross-sectional view of a conventional infrared source.

With the development of gas analyzers using different sized sample cells having different optical apertures, such as the two different sample cell configurations illustrated in FIGS. 5A–5C and 6A–6C, a need exists to reduce the source energy lost in the sample cell and the associated loss in signal level measured by the radiation detector. The present inventors observed that the desire to use different sample cell configurations interchangeably with the same transducer raised two measurement problems: a reduction in the infrared radiation received by the detectors, i.e., source efficiency, for small aperture sample cells, and a shift in data/reference ratio, previously referred to as the "bias" problem, when different airway apertures are used.

In investigating the cause of the "bias", it was determined that different sized apertures alter the mix of ray angles in the bundle of rays received at the NDIR detector assembly, which is comprised of a narrow band filter and a detector. A DIR system does not use narrow band filters. However, they are subject to a type of "bias" in that a change in angular distribution will change the width of the absorption peak. In the NDIR system, different sized apertures change the mix of incident angles at the narrow-band filter just before the infrared detector. These filters are typically of the interference type, manufactured to provide a suitably narrow selection of wavelengths for gas measurement.

Interference filters consist of multiple thin layers of dielectric material having different refractive indices and are wavelength-selective by virtue of the interference effects that take place between the incident and reflected rays at the thin-film boundaries. However, the center wavelength of interference filters shifts toward shorter wavelengths as the angle of incidence of incoming rays increases. The result of this shift is that the average passband of the filter that selects the absorption line for the gas to be measured, such as carbon dioxide, shifts as the average ray incidence angle changes. This effect can be prevented if the optical system is designed such that the angular mix does not change when the airway apertures are changed. In particular, if the system is designed so that the bundle of rays that are directed to the detector are entirely contained within the smallest apertures of interest, then there is no change if larger apertures are used.

In the case of small aperture adapters, mirror light sources, as known in the art could not be used, because the structure, or web, that holds the radiation emitter in front of the mirror is close to the same diameter as the adapter aperture. This source support structure effectively blocks light reflected from the mirror from entering the aperture. Previous optical systems known in the art, based on a reflecting aspheric mirrors, were not satisfactory because the beam emanating from the mirror assembly was larger than the smaller entrance apertures of interest. If the mirror is made smaller to match the smallest aperture, the radiation emitter support web absorbs or otherwise prevents a larger fraction of radiation from entering the smaller adapter. It is well known in the art that such a mirror can provide a better image than a spherical lens, and have a larger numerical aperture than any lens.

The present invention replaces the mirror assembly in a conventional transducer with a type of hemispherical or spherical lens, known as ball lens or half-ball lens, and reorients the radiation emitter. The emitter that had been facing and directing radiation to the mirror in a conventional gas measuring system is turned around to face the sample cell, with a ball or half-ball lens disposed between the emitter and the sample cell.

Ball lenses are well known in the telecommunication art for improving signal coupling between optical fibers and emitters and detectors, but not in the gas measurement art. A larger diameter lens is used to provide a beam that is much larger than in the pervious optical fiber case, and at the same time, the larger lens makes it possible to reduce the optical magnification while maintaining the numerical aperture (defined for any ray as the sine of the angle made by that ray with the optical axis multiplied by the index of refraction). The result of these changes is a much improved image, i.e., a better collection efficiency, at the detector. Because the beam is smaller than or equal to the smallest aperture of interest, there will be no change in the angular structure of the beam if larger apertures are used. For good emitter efficiency, the lens must have a high numerical aperture on the emitter side.

Typically, lens types manufactured for the mid-IR range, where the absorption of many gases of interest are situated, are expensive. This is the case because either the materials, such as Germanium, CaF, or ZnSe are expensive, or the lens manufacturing process is labor-intensive. However, sapphire ball lenses, in small sizes, are relatively inexpensive, because the manufacturing process is similar to that of ball bearings, and they are manufactured in high quantities for various optical, mechanical, and other non-optical purposes. Such manufacturing processes provide excellent surface uniformity, polish, and size accuracy, all a low cost. Therefore, the ball lens approach of the present invention also provides a smaller and lower cost source package, and eliminates the source web, thereby increasing the signal level.

In the present invention, a ball or half-ball is used to obtain a focal length that is suited for an infrared gas analyzer. However, a problem associated with ball or half-ball lenses with a high numerical aperture is the optical distortion inherent in such lens caused by their spherical shape, known as spherical aberration. The result of spherical aberration is a reduction in the efficiency of the collection of light at the detector. This optical defect is caused when rays of light passing through the curved surface of a lens near its edge converge at a point closer to the lens than those passing through or near its center. These edge light rays would then spread out, thereby missing the detector assembly.

A solution to this reduction in signal due to spherical aberration can be found in the present invention's design of the small aperture sample cell. The sample cell has a small volume through which gas flows. This volume is physically constructed in the form of a tube, with an optical aperture at each end. The inside walls of the tube are reflective in the wavelength band of interest, so that the tube effectively becomes a light pipe. Infrared sample cells known in the art do not have a structure and/or materials conducive to light guide properties. As a result, significant source energy is lost, and the signal/noise is poor. When using materials that are reflective in the infrared band of interest in the hollow sample cell, the walls of the sample cell tend to act like a hollow optical light pipe.

The reflective walls in the sample cell of the present invention may be obtained by coating the walls with aluminum, gold, or other metals that are highly reflective at NIR wavelengths. This can be accomplished, for example, by plating, sputtering, or any other technique known in the art. The wall surface can also be formed from a high index material. Furthermore, the walls in the sample cell can be formed from a mirror-smooth material, i.e., a material having a smooth surface void of defects, so long as the mirror-smooth material reflects strongly at relatively large incident angles. The addition of the light guide function by reflective walls improves the detector signal, and, hence improves the signal/noise by several times. As an added benefit, the rays that bounce one or more times add randomness to the light beam, thereby reducing effects of misalignment or asymmetric elements. While this approach does not correct for optical distortion caused by spherical aberration, it compensates for the reduced collection efficiency by bringing the bundle of light rays closer to the detector so that much fewer rays are lost. That is, it improves the collection efficiency, not image quality.

In addition to the cylindrical structure described above, other light guide structures may be feasible and desirable for use in the sample cell of the present invention. For example, the present invention contemplates forming the light guide in the shape of a "U", with the source and detector on the same side of the system. The light path would then be double length for the same sample cell thickness, or the sample cell could be made half as thick for the same light path length. The present invention also contemplates forming the light guide in a "C" shape, with the source and detector placed back-to-back. In addition, a detector port can be placed at the bottom of the "U" or at the back of the "C". This extra port provides a half sensitivity signal for instances where the gas of interest is otherwise so absorptive that meaningful resolution is lost. This method could also work with other optical designs (for example curved tubes either flexible or rigid) to further optimize flow characteristics without imposing on signal resolution.

In the absence of the features of the present invention, rays entering at a relatively large angle relative to the optical axis may be stopped by the aperture at the detector end of the sample cell. In practice, the length to cross section ratio is large, so that a relatively small number of rays are able to get though to the detector. The present invention contemplates that the walls of the cell are made reflective, and the cross section of the cell is made substantially equal to, or smaller than, the detector aperture. With this introduction of reflective walls, all rays that enter the sample cell at an angle that would have been stopped by the detector aperture instead are reflected off the walls at least once, and are thereby guided to pass through the aperture.

The development of products that require a changeable reduction in adapter volume, which in turn require a changeable reduction in the optical aperture as well, generate competitive pressures to reduce the cost of goods and size of gas analyzers, have spurred research into solving problems known in the art. These problems include the observed differences between difference types of sample cells, the "bias" problem, and decreased signal level for the small tube or small sample cell designs. The knowledge that good light collection is important, not good image, plus the realization that the "bias" problem is due to variations in beam Numeral Aperture motivated the present inventor to produce a sample cell having reflective side walls and to use the ball or half-ball lens in the radiation emitter.

Figure 2:
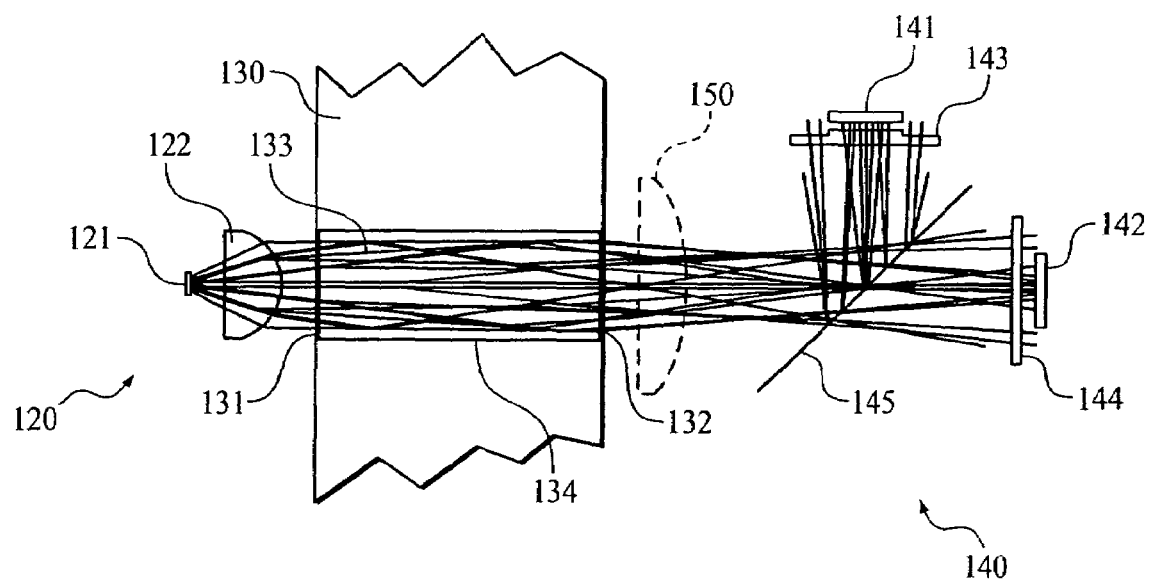
FIG. 2 is a schematic diagram of the general optical arrangement for the small tube-type airway adapter according to the principles of the present invention.

FIG. 2 schematically depicts a sample cell 130 with an infrared radiation source assembly 120 and an infrared radiation detector assembly 140. Infrared radiation source 120 comprises an emitter 121 and a half-ball lens 122. Emitter 121 emits rays of infrared radiation. These rays are collected by half-ball lens 122 and exit in a "parallel" fashion from the lens. The rays enter sample cell 130 through an entrance window 131, which is transmissive in the infrared range, and then passes through a portion of the flow path within the sample cell.

FIG. 2 schematically depicts a sample cell design in which the rays are constrained to a tube 134 having internal walls that are inherently reflective to the rays by the selection of the material forming the walls of the tube. Within the tube, a typical light ray bundle 133 is shown. The rays leave the sample cell via an exit window 132.

An optional positive lens 150, manufactured from silicon in the preferred embodiment, is disposed adjacent to exit window 132. Lens 150 reduces the size of the ray bundle at the detector, i.e., focuses the rays, so that a relatively large number of rays reach infrared detector assembly 140 thereby improving the detection efficiency, i.e., directs the more divergent light rays into the detector. Lens 150 has a relatively low numerical aperture, and is inexpensive and has both an optical function and a mechanical function. Mechanically, lens 150 is a flat-surface window that protects the elements of the detector assembly. Optically, lens 150 is a lens that reduces the magnification of the optical system, so that the source image at the detector plane is smaller, i.e., more nearly the size of the detectors, which improves the sensing ability of the detectors. In fact, the image is less than half what it would be without lens 150.

Ordinarily, magnification would be reduced by shortening the source-to-detector distance, but this is not possible in some cases, because a sample cell typically has fixed minimum distance. The only other way to reduce magnification is to increase the emitter to ball lens distance. However, if this is done, the ball lens would be larger and cost more, the beam may be too large for the tube aperture so that less emitter light is collected, resulting in an undesirable decrease in the signal output by the detector.

In the embodiment shown in FIG. 2, the infrared detector assembly comprises a beam splitter 145 that transmits and reflects a portion of the received radiation. The received radiation that is transmitted through the beam splitter passes to a reference band-pass filter 144 and is then measured by a reference detector 142. The received radiation that is reflected by the beam splitter passes to data band-pass filter 143 and is then measured by a data detector 141. While a design known as a coaxial configuration is shown, other non-dispersive and dispersive designs may be used with the half-ball lens source and reflective sample cell surfaces.

Figure 3:
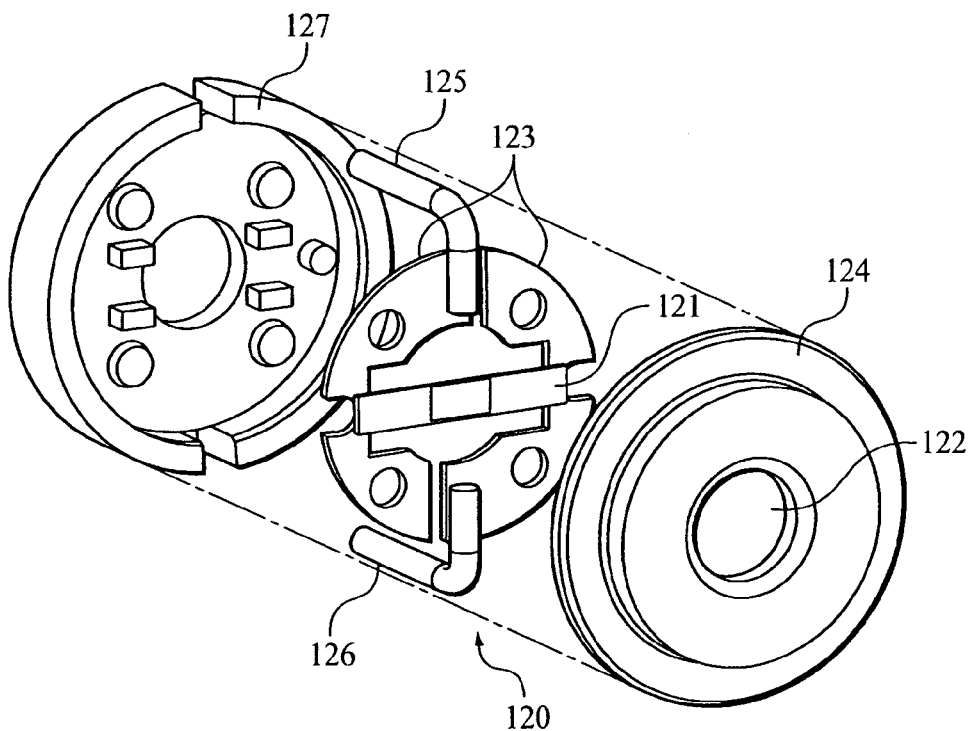
FIG. 3 is an exploded perspective view of the infrared source of FIG. 2.

FIG. 3 is a perspective view of an exemplary source assembly 120 comprising half-ball lens 122 mounted in a lens holder 124. An infrared emitter 121 is mounted on commutators 123 and a base 127 is provided into which the other components are placed. In this embodiment, half ball lens is ⅛ inch in diameter and machined from sapphire. Other sizes of half ball-lens may be used depending upon the optical apertures. Circular protrusions in base 127 provide alignment of commutators 123 with the base. Leads 125 and 126 provide the electrical interface to the emitter.

Figure 4:
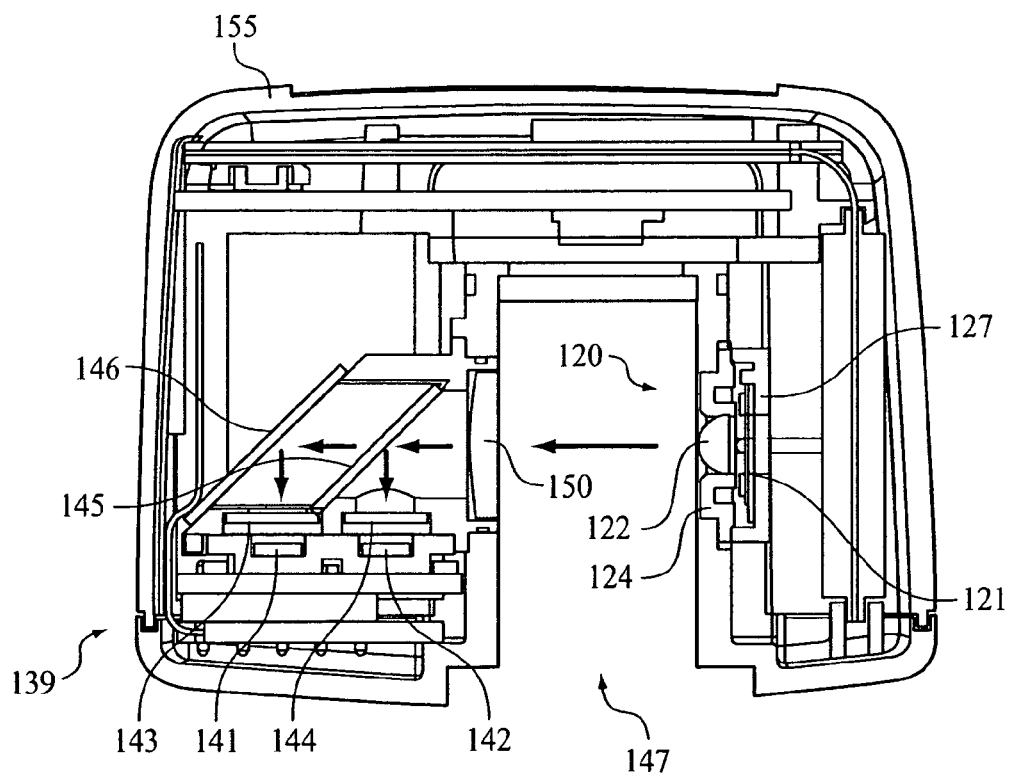
FIG. 4 is a cross-sectional view of a mainstream transducer including the infrared source of FIG. 2.

FIG. 4 depicts a cross-sectional view of an exemplary mainstream gas analyzer transducer 137 with a coaxial NDIR detector assembly 139 utilizing the source assembly of FIGS. 2 and 3. A housing 155 contains source assembly 120 and detector assembly 139. The source assembly includes half ball lens 122, lens holder 124, infrared emitter 121, and base 127. The detector assembly includes reference and data detectors 141 and 142, respectively, reference and data filters 143 and 144, respectively, beamsplitter 145 and mirror 146. As generally illustrated by the arrows in FIG. 4, infrared radiation emanating from source assembly 120 passes through the windows and the sample chamber of a sample cell that has been secured within a recess 147. After having passed through the sample cell, the radiation is split by beam splitter 145 so that radiation is directed to reference and data detectors 141 and 142. Signals from reference and data detectors 141 and 142 are amplified, filtered, and processed by electronics located in the transducer and communicated to a host system (not shown). Exemplary sample cells that are adapted to be removably securable to mainstream gas analyzer transducer 137 are described in U.S. Pat. Nos. 5,693,944, and 5,616,923 to Rich et al. and shown in FIGS. 5A–6C. As shown in FIGS. 5A–6C, the sample cell includes a transducer mounting recesses 163a and 163b (FIG. 5B) and 175a and 175b (FIG. 6B) provided on opposite sides of the sample cell. Such transducer mounting recesses provide a support surface for the transducer on the sample cell and serve to correctly align the optical components in the transducer with the sample cell.

FIGS. 5A–5C and 6A–6C depict mainstream sample cells with different optical apertures that are capable of being securably and removably coupled with mainstream gas analyzer transducer 137 of FIG. 4. Such mainstream sample cells are molded to close tolerances because the intensity of the infrared radiation impinging upon the infrared radiation detector is dependent upon the length of the optical path between radiation source and detector, and the length of that path is controlled by the width of the sample cell. Consequently, unless close tolerances are maintained, calibration of each individual sample cell would be required, which is impractical and economically prohibitive. Furthermore, sample cells of the illustrated configuration are fabricated from polymers such as polycarbonate and are relatively inexpensive.

Figure 5A:
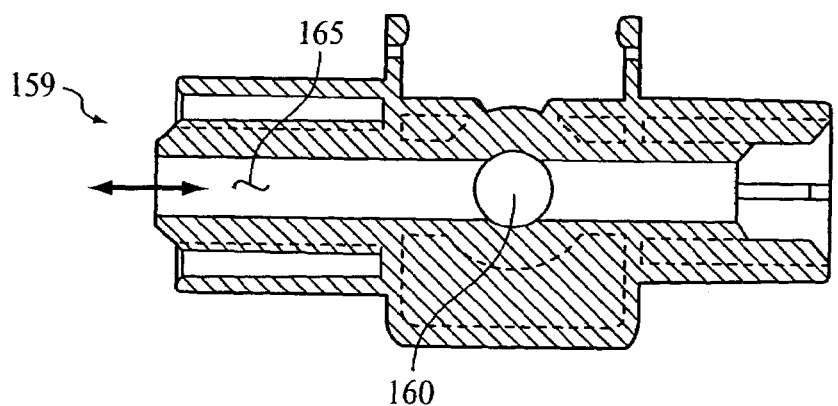
FIG. 5A is a side sectional view of a mainstream neonatal sample cell.
Figure 5B:
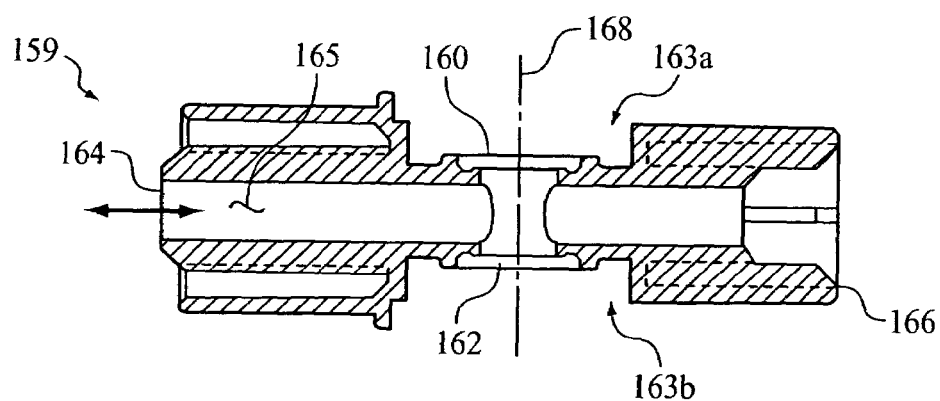
FIG. 5B is a top sectional view of the mainstream neonatal sample cell of FIG. 5A.
Figure 5C:
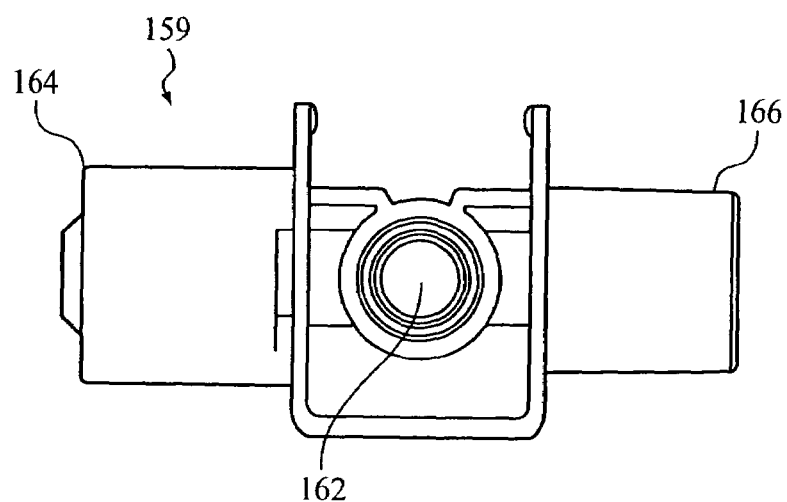
FIG. 5C is a side view of the mainstream neonatal sample cell of FIGS. 5A and 5B.

FIGS. 5A–5C depict a mainstream low deadspace sample cell 159 primarily used to monitor neonatal patients. Sample cell 159 includes a first end 164 that connects the sample cell to the patient via an endotracheal tube or other form of patient interface. A second end 166 of sample cell 159 connects to a breathing circuit. During patient inspiration, the gas flows from second end 166 through the sample cell and exits first end 164. During patient expiration, the gas flow from first end 164 through the sample cell and exits second end 166. Windows 162 and 160 located in the optical apertures of the sample cell permit the infrared radiation to pass through a flow passageway 165 of the sample cell. Line 168 indicates the centerline of the optical aperture as well as the axis for the optical path for radiation passing through the sample cell. For the embodiment shown in FIGS. 5A–5C, the infrared radiation emitted by a radiation source passes through one of the windows and traverses the sample cell substantially normal to the flow of gas within flow passageway 165 before exiting through the window disposed on the opposite side of the sample cell and entering the infrared radiation detector.

Figure 6A:
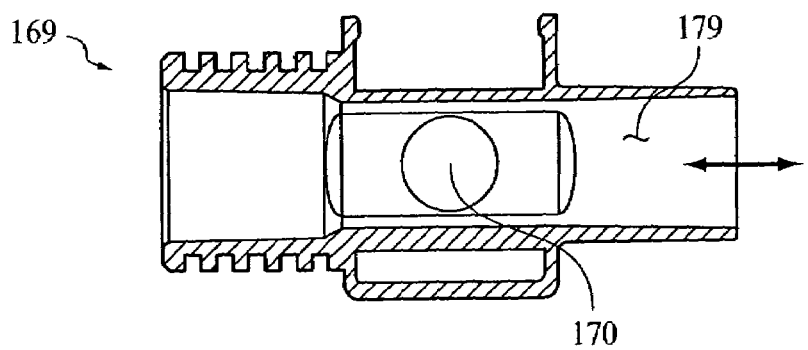
FIG. 6A is a side sectional view of mainstream pediatric/adult sample cell.
Figure 6B:
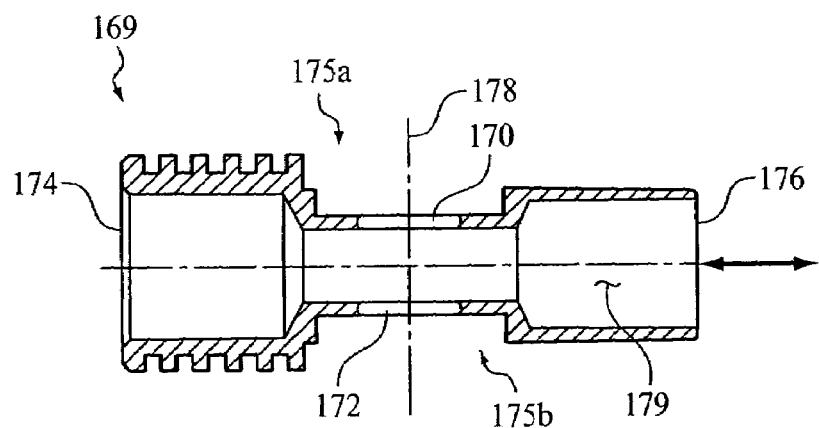
FIG. 6B is a top sectional view of the mainstream pediatric/adult sample of FIG. 6A.
Figure 6C:
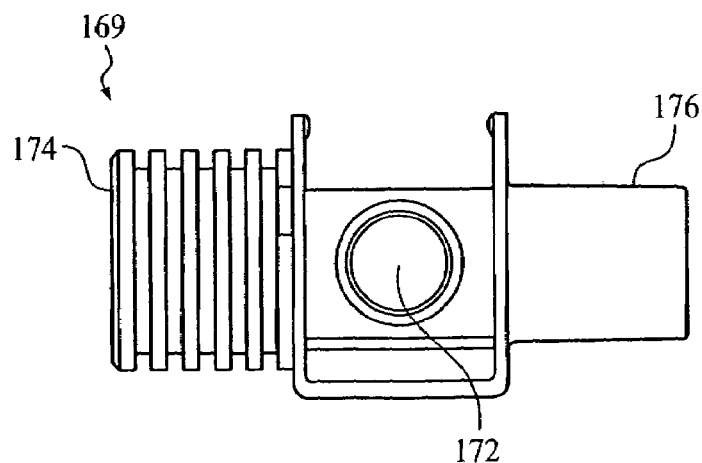
FIG. 6C is a side view of the mainstream pediatric/adult sample cell of FIGS. 6A and 6B.

FIGS. 6A–6C depict a mainstream sample cell 169 primarily used to monitor pediatric and adult patients. Sample cell 169 includes a first end 174 that connects the sample cell to the patient via an endotracheal tube or other form of patient interface. A second end 176 of sample cell 169 typically connects to a breathing circuit. During patient inspiration, the gas flows from second end 176 through the sample cell and exits first end 174. During patient expiration, the gas flows from first end 174 through the sample cell and exits second end 176. Windows 172 and 170 located in the optical apertures of the sample cell permit the infrared radiation to pass through the flow passageway of the sample cell. Line 178 indicates the centerline of the optical aperture as well as the axis for the optical path for radiation passing through the sample cell. For the embodiment shown in FIGS. 6A–6C, the infrared radiation emitted by a radiation source passes through a window and traverses the sample cell along an optical path corresponding to line 178 that is substantially normal to the flow within a flow passageway 179 before exiting through the window disposed on the opposite side of the sample cell and entering the infrared radiation detector.

Figure 7:
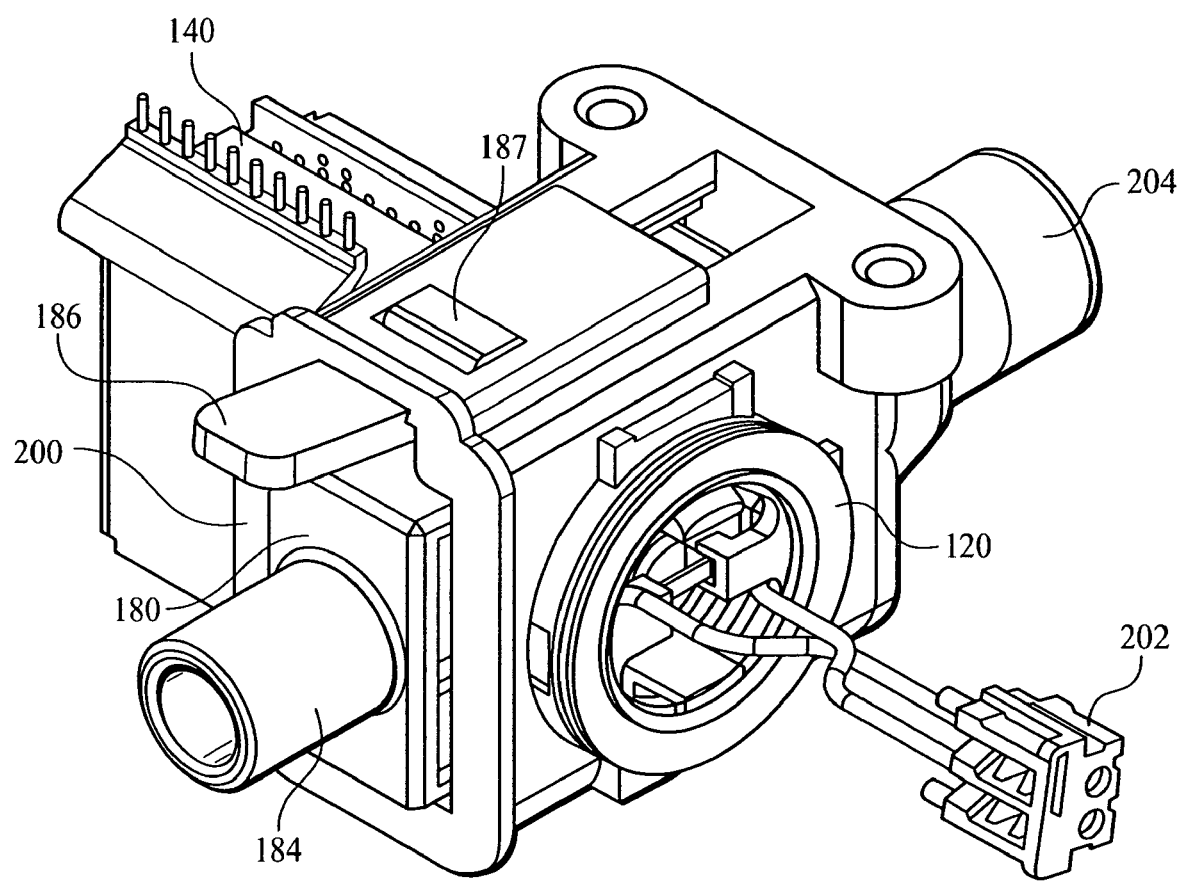
FIG. 7 is a perspective view of a sidestream sample cell receptacle and measurement optics.

FIG. 7 is a perspective view of a sidestream sample cell receptacle 200 and the gas measurement optics associated therewith. Detector assembly 140 and source assembly 120 are affixed to sample cell receptacle 200. A sample cell 180 is shown in the "latched" or engaged position in the sample cell receptacle, with a protrusion 187 of a latching arm 186 extending from a sample cell securely engaged in a slot defined in sample cell receptacle 200. A sample cell output port (not shown) seats to a seal disposed within an input port 204 attached to the sample cell receptacle. Source assembly 120 is used in the embodiment shown and comprises the half ball lens, lens holder, infrared emitter, and base.

Figure 8:
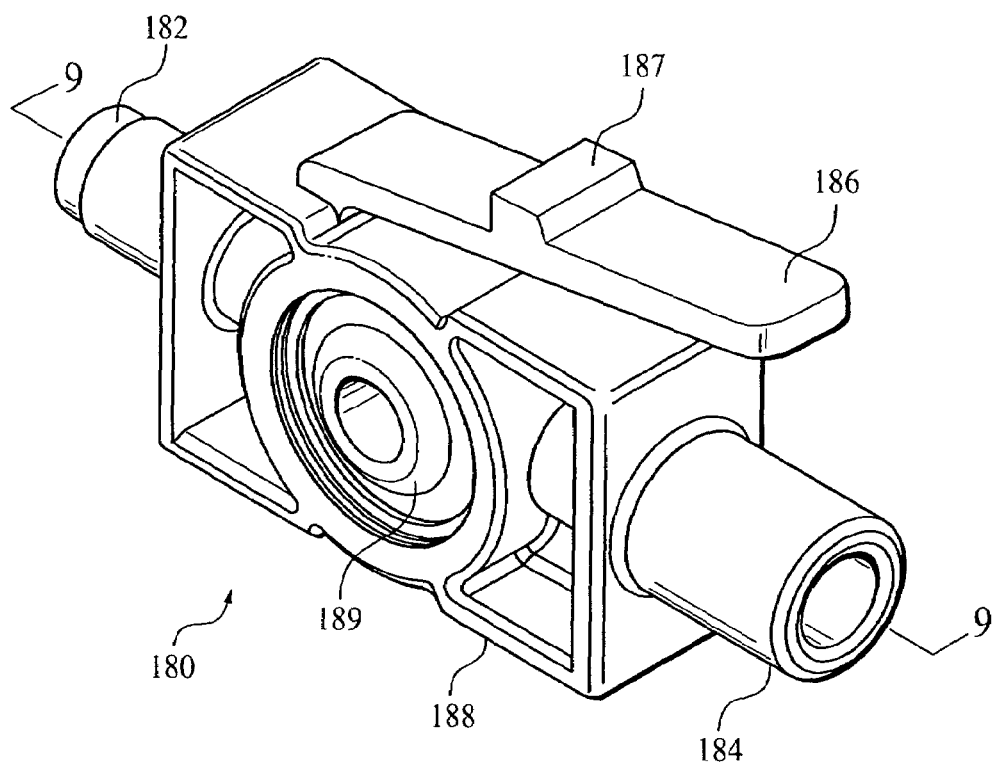
FIG. 8 is a perspective view of the sample cell body with the sample cell core inserted therein.

FIG. 8 schematically illustrates an exemplary embodiment of sample cell 180 according to the principles of the present invention. Sample cell 180 includes a sample cell body or housing 188 and a sample cell core 189 that is removeably attached within a chamber defined in the sample cell body. Gas from a sampling tubing originating in an airway adapter or nasal cannula is drawn through an optional filter prior to entering sample cell body 180 via an inlet port 184. Infrared radiation is passed through the gas flowing through sample cell 180, and a portion of the infrared radiation is absorbed by the gases present in the sample cell. Using an optics configuration coupled to this sample cell, the partial pressure of gases, such as carbon dioxide, can be measured. The gas exits sample cell body 188 via an output port 182 and into a pump prior to exiting via an exhaust or scavenging port. Sample cell 180 is optically and mechanically coupled with a radiation source assembly and a radiation detection assembly. The radiation is emitted from source assembly 120, then passes through sample cell 180 and enters infrared radiation detection assembly 140.

Sample cell 180 may be positioned either temporarily or permanently within the measurement optics, which includes a radiation source assembly and radiation detector assembly. The infrared radiation from source assembly passes through a window (not shown) of sample cell body 188 into the interior of sample cell core 189, where a portion of the radiation is absorbed by the gas in the sample cell core. The transmitted radiation then may either pass through another window (not shown) or reflect and pass again through the window. A window may be secured to sample cell body 189 via a snap-in retainer ring. In either case, a detector assembly eventually converts the transmitted radiation into signals that are sampled and converted into a measured value.

Figure 9:
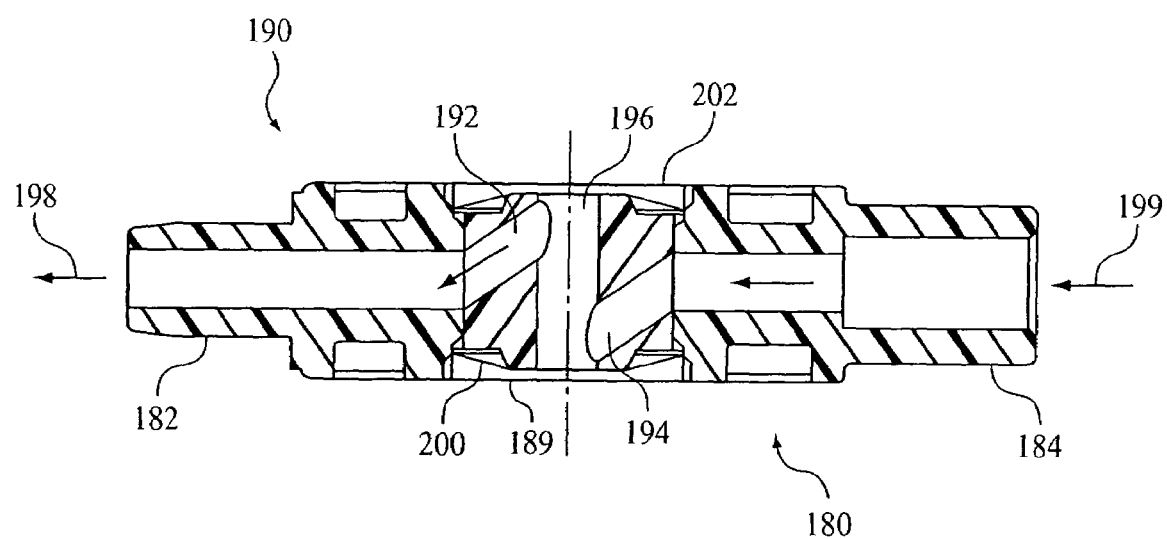
FIG. 9 is a cross-sectional view of the sample cell body and sample cell core taken along line 9—9 of FIG. 8.

FIG. 9 is a cross-sectional view of the exemplary sample cell 180 taken substantially along line 9—9 of FIG. 8. A flow of gas through passages within sample cell body 188 and sample cell core 189 are indicated by arrows 198 and 199. More specifically, gas enters the sample cell after passing through the sampling tubing and an optional filter device to remove fluids before entering the sample cell, as indicated by arrow 199. After the gas passes through a passage within inlet port 184, it enters the passage located within the sample cell core 189. Within sample cell core 189, the gas enters a sample chamber 196 via an inlet 194 adjacent to a window 200 at one end of the sample chamber and exits via an outlet 192 adjacent to a window 202 at the opposite end of sample cell chamber 196. Sample cell chamber 196 is the portion of the passage in which radiation passes through, and it is the infrared reflectivity of this chambers interior surfaces that enhances the signal received by the infrared detectors.

Sample chamber 196 in a preferred embodiment has a cylindrical design, with the inlet and outlet positioned at opposite ends of the sample chamber as close to the windows as possible to permit the sample gas to cleanly pass through the sample cell without crevices and other "unswept" volumes (sometimes referred to as "deadspace"). To enhance the infrared reflectively, sample cell core 189 may be molded from a high index material or sample cell chamber 196 may be plated with a material that is highly reflective at NIR wavelengths. After passing out of sample cell core 189, the gas exits sample cell 180 after passing through the passage within outlet 182, as indicated by arrow 198. The sample cell core is preferably located in the central portion of the sample cell and provides a passage for the gas sample between the symmetrical inlet and outlet passages in the body. The optical path of sample cell 180 does not simply transverse the flow path, but is parallel with the flow path for a substantial portion of the path length. To achieve this alternative flow path and minimize the disturbance to the flow profile, a flow passage shape referred to as the "Z" configuration, is used in this exemplary sample cell. This configuration also allows for the uniform flow passage from outside the sample cell, into the sample cell body and sample cell core without unnecessary transitions and the resultant turbulence.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A system adapted to analyze a concentration of a selected gas in a gas sample, the system comprising:
   (a) a gas analyzer comprising:
      (1) a gas analyzer housing,
      (2) a receptacle defined in the gas analyzer housing,
      (3) a source disposed in the gas analyzer housing and adapted to emit radiation of a specified intensity and wavelength along an optical path such that the radiation is absorbed by the selected gas in the gas sample being analyzed, and
      (4) an infrared radiation detector disposed in the gas analyzer housing along the optical path in optical communication with the source and adapted to detect an intensity of the emitted radiation by the source after the radiation has passed through the gas sample; and
   (b) a sample cell adapted to be disposed between the source and infrared radiation detector, wherein the sample cell includes:
      (1) a sample cell housing adapted to be selectively disposed in the receptacle,
      (2) a gas inlet disposed at a first end portion of the sample cell housing and on a first side of the sample cell,
      (3) a gas outlet disposed at a second end portion of the housing generally opposite the first end portion and on a second side of the sample cell generally opposite the first side of the sample cell, and
      (4) a gas flow passage defined in the sample cell through at least a portion of the sample cell housing between the gas inlet and the gas outlet, wherein the gas flow passage is generally parallel to the optical path between the source and the detector such that the gas flow passage defines a sample chamber, wherein a length of the gas flow passage defining the sample chamber is greater than a width of the gas flow passage, and wherein the gas inlet, the gas outlet, and the gas flow passage are disposed in a "Z" configuration in which at least one angle in the "Z" configuration through which gas passes is less than 90°, and wherein at least a portion of a wall defining the gas flow passage includes an infrared reflective surface so as to direct rays of radiation from the source to the infrared radiation detector generally along the optical path.

2. The system of claim 1, wherein the infrared reflective surface is selected from group consisting of aluminum and gold.

3. The system of claim 1, wherein the infrared reflective surface comprises a high index material.

4. A system for analyzing the concentration of a selected gas in a gas sample, comprising:
   (a) a gas analyzer comprising:
      (1) a gas analyzer housing,
      (2) a receptacle defined in the gas analyzer housing,
      (3) a source disposed in the gas analyzer housing and adapted to emit radiation of a specified intensity and wavelength such that the radiation is absorbed by the selected gas in the gas sample being analyzed,
      (4) a high numerical aperture-lens disposed in the gas analyzer housing so as to receive radiation from the source and direct the emitted rays in a manner to be substantially parallel to each other, and
      (5) an infrared radiation detector disposed in the gas analyzer housing in optical communication with the emitter and adapted to detect an intensity of the emitted radiation by the source after the radiation has passed through the gas sample; and
   (b) a sample cell disposed between the source and the infrared radiation detector, wherein the sample cell includes:
      (1) a sample cell housing adapted to be selectively disposed in the receptacle,
      (2) a gas inlet disposed at a first end portion of the sample cell housing,
      (3) a gas outlet disposed at a second end portion of the sample cell housing, and
      (4) a gas flow passage is defined in the sample cell through at least a portion of the sample cell housing between the gas inlet and the gas outlet, wherein the gas flow passage is generally parallel to an optical path between the source and the detector such that the gas flow passage defines a sample chamber, wherein the gas inlet, the gas outlet, wherein the gas flow passage is disposed in a "Z" configuration in which at least one angle in the "Z" configuration through which gas passes is less than 90°, and wherein a length of the gas flow passage defining the sample chamber is greater than a width of the gas flow passage.

* * * * *